US011813312B2

(12) United States Patent
Thomas

(10) Patent No.: US 11,813,312 B2
(45) Date of Patent: Nov. 14, 2023

(54) GLUCAGON ANALOGUES AS LONG-ACTING GLP-1/GLUCAGON RECEPTOR AGONISTS IN THE TREATMENT OF FATTY LIVER DISEASE AND STEATOHEPATITIS

(71) Applicant: Boehringer Ingelheim International GmbH, Ingelheim am Rhein (DE)

(72) Inventor: Leo Thomas, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/237,210

(22) Filed: Apr. 22, 2021

(65) Prior Publication Data

US 2021/0330749 A1 Oct. 28, 2021

(30) Foreign Application Priority Data

Apr. 24, 2020 (EP) .................................. 20171285

(51) Int. Cl.
*A61K 38/26* (2006.01)
*A61P 1/16* (2006.01)

(52) U.S. Cl.
CPC ................ *A61K 38/26* (2013.01); *A61P 1/16* (2018.01)

(58) Field of Classification Search
None
See application file for complete search history.

(56) References Cited

U.S. PATENT DOCUMENTS

2020/0268835 A1   8/2020   Lau et al.

FOREIGN PATENT DOCUMENTS

| WO | 2014056872 A1 | 4/2014 | |
|---|---|---|---|
| WO | 201491316 A2 | 6/2014 | |
| WO | 2015055801 | 4/2015 | |
| WO | 2015055801 A1 | 4/2015 | |
| WO | 2015055802 A2 | 4/2015 | |
| WO | WO-2015055801 A1 * | 4/2015 | ........... A61K 31/137 |
| WO | 2017153575 A1 | 9/2017 | |
| WO | 2018100174 A1 | 6/2018 | |
| WO | 2019030268 A1 | 2/2019 | |
| WO | WO-2019030268 A1 * | 2/2019 | ......... A61K 38/2278 |
| WO | 2020173973 A1 | 9/2020 | |
| WO | 2021219543 A1 | 11/2021 | |

OTHER PUBLICATIONS

Hagstrom, Fibrosis stage but not NASH predicts mortality and time to development of severe liver disease, vol. 67, 2017.
Bedossa, Histopathological Algorithm and Scoring System, AASLD Pubs, 2012.
Younassi, Global Epidemiology of Nonalocoholic Fatty Lover Disease, ASASLD pubs, 2016.
Kristansen, Obese diet induced mouse models of nonalocoholic steaohepaitits-tracking disease, World Jouranl of Hepatology, vol. 8, 2016.
Dulai, Increased Rosk of Mortality by Fibrosis Stage in Nonalcoholic Fatty liver Disease, Hepatology, vol. 65, 2017.
Clapper, Diet induced mouse model of fatty liver disease Am. J. Physiol, vol. 35, 2013.
Neuswander-Tetri, Improved nonalcoholic steatohepatitis, AASLD pubs, vol. 38, 2003.
Zhou, Role of AMP-activated protein kinase, JCI, vol. 108, 2001.
Armstrong, Liraglutide efficacy and action in non alcoholic steatohepatits, BMJ open, 2013.
Armstrong, Linaglutide safety and efficacy in patients with non alcoholic steatohepatits, The Lancet, vol. 387. 2016.
Vadelcantos, a novel, glucagen like peptide, Hepatology, vol. 65, 2017.
Ratziu, Elafibranor, an Agonist of the Peroxisome Proliferator, Gastroenterology, vol. 150, 2016.
Cliner and Bedossa, Liver Histololgy, Hepatology, 2005.
Battaler, Liver Fibrosis, JCI. 2005.
Williams, Prevalance of No alcoholic fatty liver disease and non-alcoholic steatohepatitis, Gastroenterology, vol. 140, 2011.
Vernon, Systematic review, the epidemiology and natural history of non alcoholic fatty lover disease,Aliment Pharmacol Ther., vol. 34, 2011.
Lazo, Prevalence of non alcoholic fatty liver disease in the US, Amer, J. of Epidemiology, vol. 178, 2013.
Bertot, the natural course of non alcoholic fatty liver disease, Int. j. molecular sciences, vol. 17, 2016.
Kleiner, Design and validation of a Histological scoring system for non alcoholic fatty lover disease, Hepatology, 2005.
Gastaldelli, Amalia et al. "Time for Glucagon like peptide-1 receptor agonistss treatment for patients with NAFLD?" (2016) EASL Journal of Hepatology, 64, 262-264.
Skarbaliene, J. et al. "Exploring the therapeutic potential of glucagon/ GLP-1 receptor dual agonist ZP2929 in a mouse model of diet induced and biopsy-confirmed non-alcoholic steatohepatitis" (2017) Poster—The International Liver Congress, Apr. 1-23, Amsterdam, Netherlands, Zealand Pharma.

* cited by examiner

*Primary Examiner* — Christina Bradley
(74) *Attorney, Agent, or Firm* — Mary Breen Smith

(57) ABSTRACT

The present invention relates to the medical use of specific long-acting glucagon analogues having dual GLP-1/glucagon receptor agonist activity in the prevention and/or treatment of metabolic liver disease, particularly non-alcoholic fatty liver disease (NAFLD), non-alcoholic fatty liver (NAFL), non-alcoholic steatohepatitis (NASH), NAFLD-associated liver fibrosis and/or cirrhosis.

8 Claims, 8 Drawing Sheets

Specification includes a Sequence Listing.

a)

b)

a)

b)

c)

d)

e)

f)

GLUCAGON ANALOGUES AS LONG-ACTING GLP-1/GLUCAGON RECEPTOR AGONISTS IN THE TREATMENT OF FATTY LIVER DISEASE AND STEATOHEPATITIS

FIELD OF THE INVENTION

The present invention relates to the medical use of specific long-acting glucagon analogues having dual GLP-1/glucagon receptor agonist activity in the prevention and/or treatment of metabolic liver disease, particularly non-alcoholic fatty liver disease (NAFLD), non-alcoholic fatty liver (NAFL), non-alcoholic steatohepatitis (NASH), NAFLD-associated liver fibrosis and/or cirrhosis.

BACKGROUND OF THE INVENTION

Fatty liver disease is a chronic condition characterized by excessive hepatic triglyceride deposition. It can be due to multiple causes, the major two forms being related to immoderate alcohol consumption or metabolic dysregulation in the absence of excessive alcohol intake. The latter has been termed nonalcoholic fatty liver disease (NAFLD). It is commonly linked to the metabolic syndrome and its individual components (obesity, type 2 diabetes mellitus, dyslipidemia and hypertension). The spectrum of NAFLD ranges from isolated hepatic steatosis also referred to as non-alcoholic fatty liver (NAFL) through non-alcoholic steatohepatitis (NASH) characterized by hepatic triglyceride accumulation, hepatocellular injury and lobular inflammation, to liver fibrosis. Of note, fibrosis can be present to various degrees in patients with NASH. The presence of NASH with fibrosis is a strong risk factor for development of cirrhosis and potentially hepatocellular carcinoma (Hagstrom et al., Journal of Hepatology 2017, vol. 67, pp. 1265-1273).

NAFLD is a common condition; global prevalence has been estimated to be as high as 25% (Younossi et al, Hepatology 2016, vol. 64, pp. 73-84). Transition from NAFL as a relatively benign condition to NASH and especially progression of fibrosis have been linked to an increase in risk of overall mortality (see, e.g., Dulai et al, Hepatology 2017, vol. 65, pp. 1557-1565).

NAFLD is known to be caused by various etiologies such as insulin resistance, lipotoxicity and inflammatory responses. Among them, the most common etiology is insulin resistance.

A lot of effort has been made to improve the insulin resistance to prevent/treat non-alcoholic fatty liver disease. For example, clinical trials for thiazolidnedinones (TZD) or metformin, a kind of insulin sensitizer, have been conducted (see, Hepatology (2003) 38: 1008-17, J Clin Invest (2001) 108: 1167-74).

However, in the case of treatment with the TZD-based drugs, there are disadvantages of a large weight gain and fluid retention and thus the use of such treatment has been known to be impossible for patients with a heart disease. In addition to the TZD-based drugs, clinical tests using GLP-1 receptor agonists such as Victoza (Liraglutide) or Byetta for NAFLD have been conducted.

Liraglutide is a marketed chemically modified analogue of glucagon-like peptide-1 (GLP-1). The amino acid sequence of Liraglutide is shown as SEQ ID NO.: 1

(SEQ ID NO.: 1)
HAEGTFTSDVSSYLEGQAAK((S)-4-Carboxy-4-hexadecanoyl-amino-butyryl-)EFIAWLVRGRG Liraglutide acts as a GLP-1 receptor (GLP1R) agonist. Such GLP1R agonists have been demonstrated to lower blood glucose and reduce body weight. Moreover, treatment of patients with overweight or obesity with biopsy proven NASH with the GLP1R agonist liraglutide led to resolution of NASH in 39% of the patients, compared to 9% under placebo (Armstrong et al., BMJ Open 2013, vol. 3, e003995; Armstrong et al, Lancet 2016, vol. 387, pp. 679-690).

A pegylated synthetic analogue of oxyntomodulin, a dual agonist of GLP-1 and glucagon receptors, although with reduced affinity compared to the single agonists GLP-1 and glucagon, has been tested in a rodent model of NASH (Valdecantos et al., Hepatology 2017, vol. 65, pp. 950-968). The analogue, termed G49 and having a length of 29 amino acids, was analyzed in microarrays and liver regeneration after partial hepatectomy.

WO 2014/091316 relates to co-agonists of glucagon and GLP-1. WO 2017/153575 discloses further data of these co-agonists, including data from clinical trials of G933. The geometric mean half-life of G933 seems to be about 10 to 12 hours.

WO 2014/056872 A1 and WO 2018/100174 A1 disclose exendin-4 derivatives which activate the GLP-1 and the glucagon receptor. In these exendin-4 derivatives, among other substitutions, methionine at position 14 is replaced by an amino acid carrying an $NH_2$ group in the side chain, which is further substituted with a non-polar residue (e.g. a fatty acid optionally combined with a linker). WO 2014/056872 reports the half-life in mice of some exendin-4 derivatives (Example 10, Table 6). The reported values are all below 4 h. Further information, e.g. from a murine diet-induced NASH model, of some compounds are provided in WO 2019/030268.

WO 2015/055801 and WO 2015/055802 disclose glucagon analogue peptides having increased selectivity for the GLP-1 receptor as compared to human glucagon. Methods for the treatment of obesity, excess weight and diabetes on the basis of these peptides are also disclosed.

Simultaneous activation of the GLP-1 and glucagon receptor is expected to decrease food intake and increase energy expenditure and is expected to result in weight loss in patients with obesity or overweight. While glycemic control is provided by the GLP-1 receptor agonistic property, food intake is reduced by both receptors and energy expenditure is increased by glucagon receptor agonism. The combination of the effects on food intake and energy expenditure is expected to result in a longer lasting negative energy balance than with pure GLP-1 receptor agonists and to lead to robust weight loss and improvement in NASH. The balance of GLP-1 and glucagon receptor activation is hypothesized to be the key factor for achieving weight loss and maintenance in the presence of a favorable benefit-risk profile, as well as improving NASH.

However, as for the compounds mentioned above, the in vivo half-life is short, and thus administrations must be repeated frequently, e.g. once per day. There is a disadvantage due to inconvenience to patients as these administrations are usually done subcutaneously. Such frequent administrations cause pain and discomfort to patients.

No pharmacologic treatment of a condition pertaining to the spectrum of NAFLD has been approved by the medical authorities so far. Thus, a high need exists to identify new, safe, and effective compounds that can slow down, stop or reverse the time course of NAFLD (incl. NASH) progression, or the progression towards advanced fibrosis and/or cirrhosis.

Further, there is a need for treatment for NAFLD (including NASH) that comprises administration of a (long acting) medicament that needs to be administered less frequently (e.g. weekly). At the same time, the treatment should still be effective, e.g. as determined by the NAFLD activity score or other relevant biomarkers (e.g. liver fat content reduction or change of liver enzymes).

The compounds for the use in treatment as disclosed herein have the potential to be administered less frequently and still be effective.

SUMMARY OF THE INVENTION

Provided herein is the medical use of specific long-acting dual GLP-1/glucagon receptor agonists in the prevention and/or treatment of metabolic liver disease, like non-alcoholic fatty liver disease (NAFLD), particularly non-alcoholic fatty liver (NAFL), non-alcoholic steatohepatitis (NASH), NAFLD-associated liver fibrosis and/or cirrhosis.

WO 2015/055801 discloses peptidic compounds derived from glucagon that (unlike native glucagon) potently activate both the GLP-1 and the glucagon receptor.

It now was found that glucagon analogues of formula I having dual agonist activity may effectively be used in the treatment of specific liver diseases like NAFLD, particularly NASH. All compounds of formula I are structurally closely related, having a length of 29 amino acids, an amidated C-terminus, and sharing an overall identity of 22 amino acids.

Accordingly, the present invention is directed to a compound (including salts) having the general formula I R—H-X2-QGTFTSDYSKYL-X15-X16-X17-X18-
AKDFI-X24-WLE-X28-A-NH$_2$(SEQ ID NO.:2)   (I)

wherein
R is selected from H, C$_{1-4}$ alkyl and acetyl;
X2 is selected from Aib and Ac4c;
X15 is selected from Asp and Glu;
X16 is selected from Glu and Ψ;
X17 is selected from Arg and Ψ;
X18 is selected from Ala and Arg;
X24 is selected from Glu and Ψ;
X28 is selected from Ser and Ψ;
wherein the compound contains one and only one Ψ and wherein said Ψ is a residue of Lys, in which the amino group of the side chain is conjugated to a substituent selected from the group consisting of
HOOC—(CH$_2$)$_{16}$—(CO)-isoGlu-Peg3-Peg3-, and
HOOC—(CH$_2$)$_{16}$—(CO)-isoGlu-GSGSGG-, for use in a method of preventing and/or treating metabolic liver disease, particularly for treating NAFLD, NASH and/or cirrhosis.

In a more specific embodiment, the present invention is directed to a compound selected from (Compound 1, SEQ ID NO.: 3)
H-H-Aib-QGTFTSDYSKYLD-K([17-carboxy-heptadecanoyl]- isoGlu-Peg3-Peg3)-RAAKDFIEWLESA-NH$_2$ (Compound 2, SEQ ID NO.: 4)
H-H-Aib-QGTFTSDYSKYLDERAAKDFI-K([17-carboxyheptadecanoyl]-isoGlu-GSGSGG)-WLESA-NH$_2$ (Compound 3, SEQ ID NO.: 5)
H-H-Ac4c-QGTFTSDYSKYLDE-K([17-carboxyheptadecanoyl]-isoGlu-Peg3-Peg3)-RAKDFIEWLESA-NH$_2$ (Compound 4, SEQ ID NO.: 6)
H-H-Aib-QGTFTSDYSKYLE-K([17-carboxy-heptadecanoyl]- isoGlu-GSGSGG)-RAAKDFIEWLESA-NH$_2$ (Compound 5, SEQ ID NO.: 7)
H-H-Ac4c-QGTFTSDYSKYLDERAAKDFI-K([17-carboxyheptadecanoyl]-isoGlu-GSGSGG)-WLESA-NH$_2$ (Compound 6, SEQ ID NO.: 8)
H-H-Ac4c-QGTFTSDYSKYLDERAAKDFIEWLE-K([17-carboxyheptadecanoyl]-isoGlu-GSGSGG)-A-NH$_2$ for use in a method or preventing and/or treating NAFLD, NASH and/or cirrhosis.

Further aspects and embodiments of the present invention will become apparent from the disclosure below.

Figure 1:
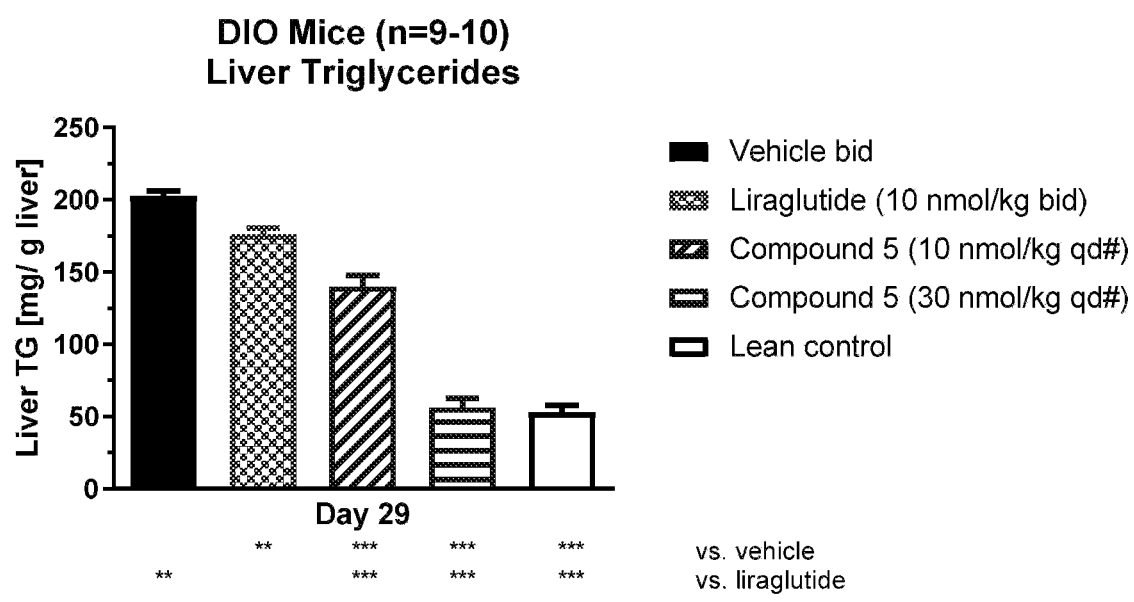
FIG. 1(a) shows the reduction of liver steatosis in DIO mice/liver triglycerides (Example 1).
FIG. 1(b) shows the lowering of ALT in plasma in DIO mice/ALT.
Figure 1:
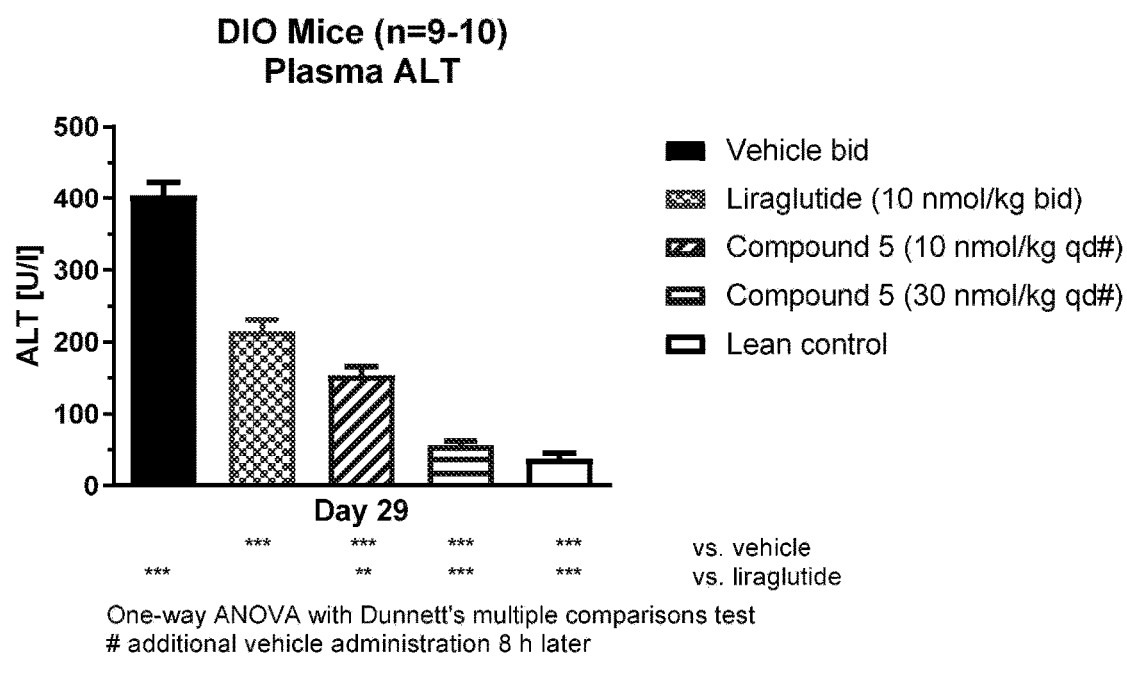

For both FIGS. 1(a) and 1(b), statistical analyses were performed by one-way ANOVA followed by Dunnett's multiple comparisons test. Significant differences are indicated by asterisks (, $p<0.01$; *, $p<0.001$).

FIG. 2(a) through FIG. 2(f) show the effect of treatment with compound 5 (SEQ ID NO.: 7) at doses of 80 μg/kg, 120 μg/kg and 160 μg/kg (qd), and liraglutide at a dose of 400 μg/kg qd over eight weeks in mice with AMLN-diet-induced NASH, compared to vehicle-treated control animals on the same diet. (Example 2).

Figure 2:
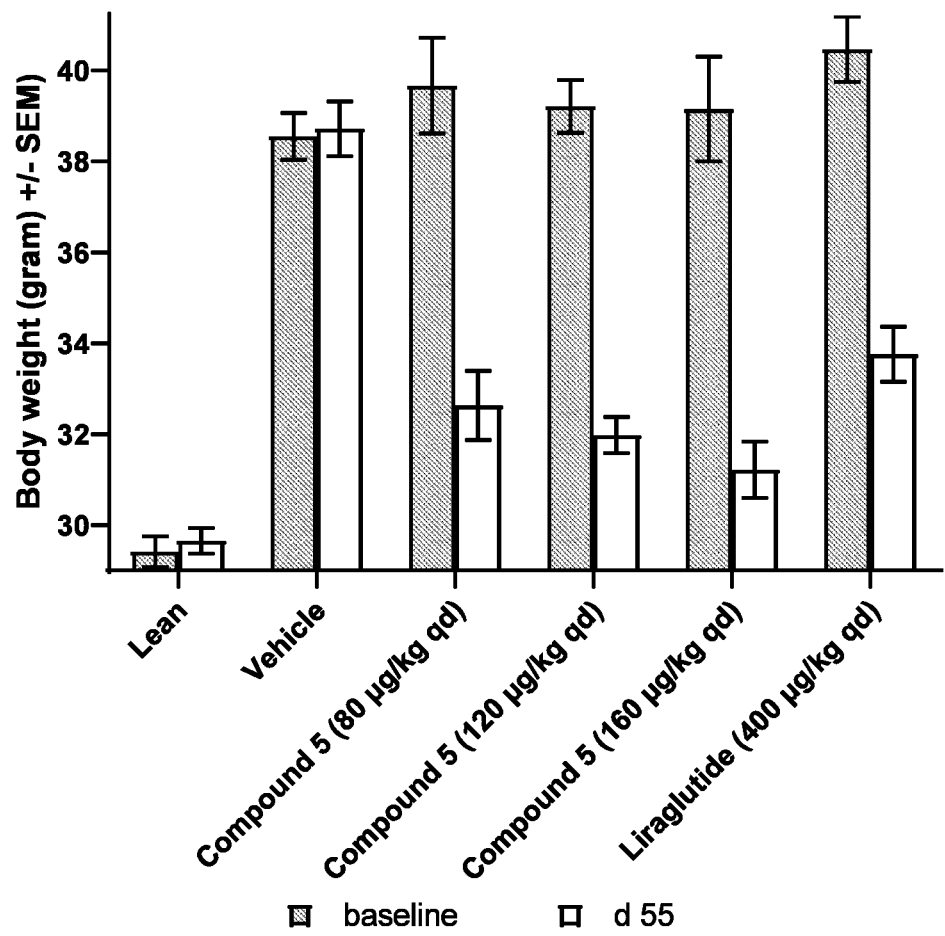
Figure 2:
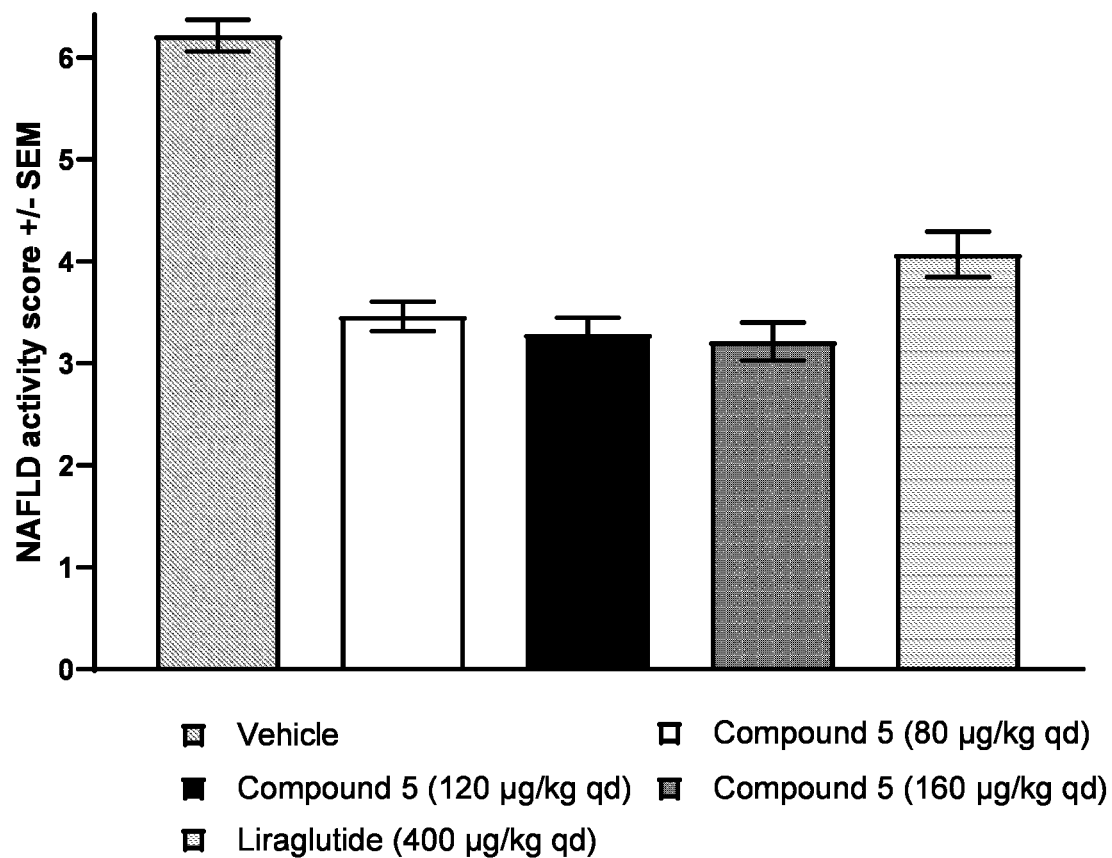
Figure 2:
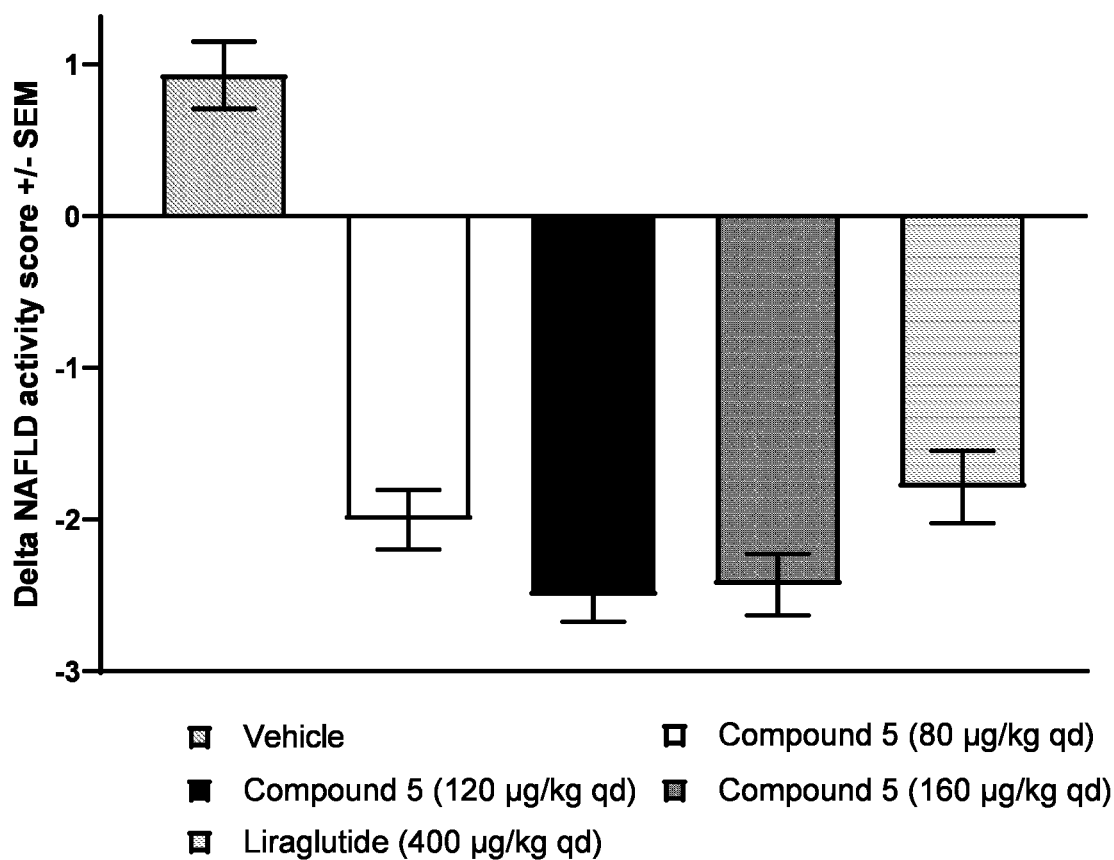
Figure 2:
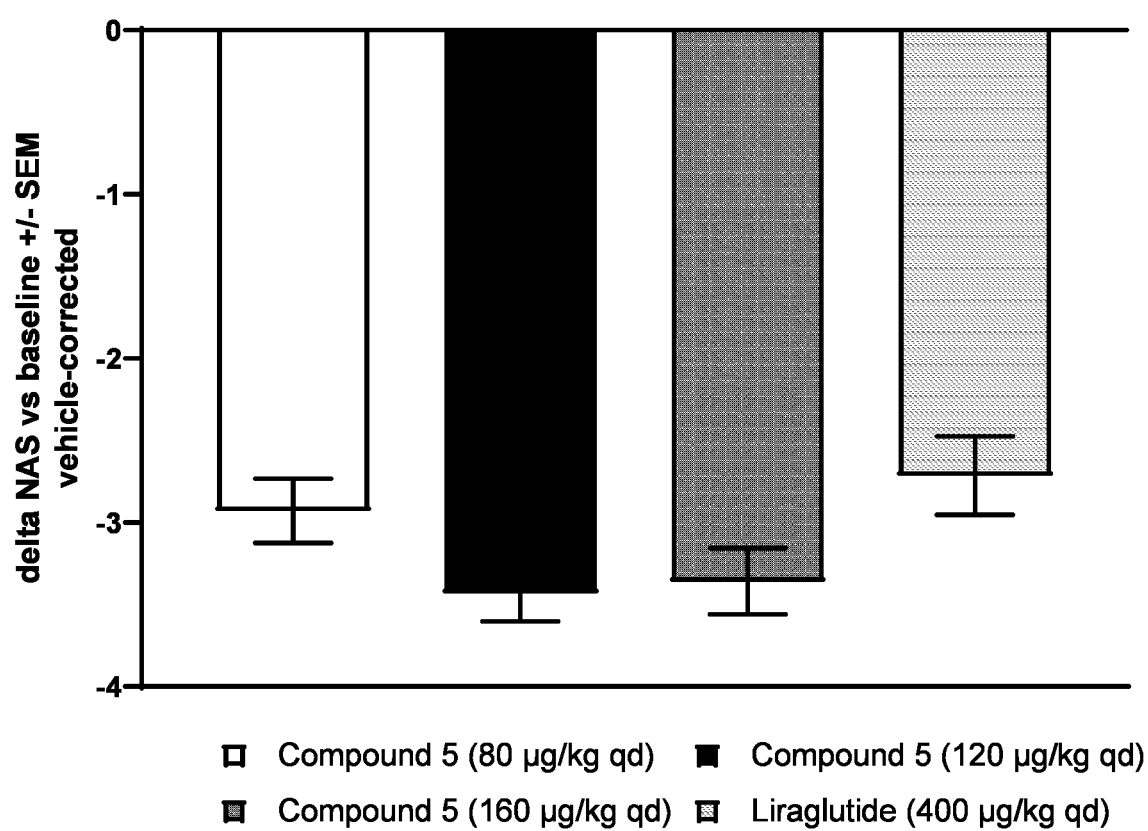
Figure 2:
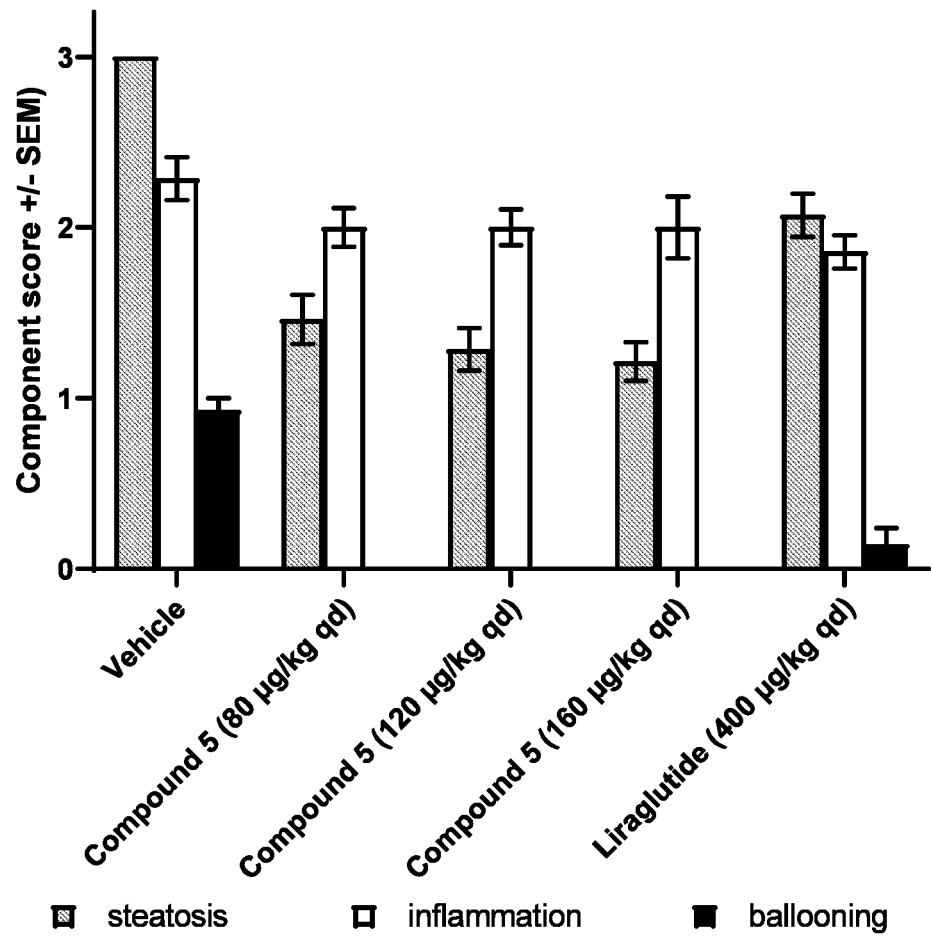
Figure 2:
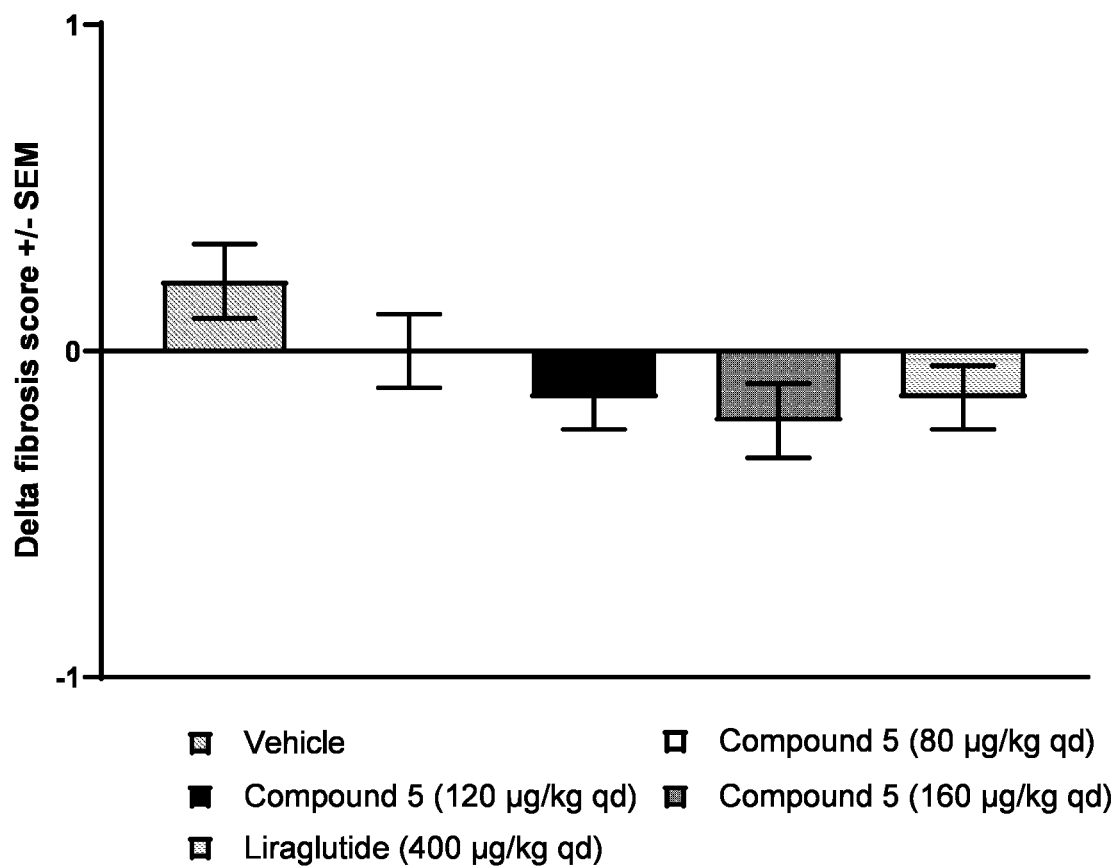

FIG. 2(a) shows the body weight at baseline and after 55 days of treatment.

FIG. 2(b) shows the Overall NAFLD activity score after termination of treatment on day 56.

FIG. 2(c) shows the change in NAFLD activity score (pre-biopsy before start of treatment vs. biopsy after treatment.

FIG. 2(d) shows the change in NAFLD activity score (vehicle corrected).

FIG. 2(e) shows the components of the NAFLD activity score (hepatic steatosis, lobular inflammation, hepatocyte ballooning) at the end of the study.

FIG. 2(f) shows the change in fibrosis score.

DETAILED DESCRIPTION OF THE INVENTION

As mentioned above, the present invention is directed to a compound having the general formula I:

R—H-X2-QGTFTSDYSKYL-X15-X16-X17-X18-
AKDFI-X24-WLE-X28-A-NH$_2$(SEQ ID NO.:2)   (I)

wherein
R is selected from H, C$_{1-4}$ alkyl and acetyl;
X2 is selected from Aib and Ac4c;
X15 is selected from Asp and Glu;
X16 is selected from Glu and Ψ;
X17 is selected from Arg and Ψ;
X18 is selected from Ala and Arg;

X24 is selected from Glu and Ψ;

X28 is selected from Ser and Ψ;

wherein the compound contains one and only one Ψ and wherein said Ψ is a residue of Lys, in which the amino group of the side chain is conjugated to a substituent selected from the group consisting of HOOC—$(CH_2)_{16}$—(CO)-isoGlu-Peg3-Peg3-, and HOOC—$(CH_2)_{16}$—(CO)-isoGlu-GSGSGG-, for use in a method of preventing or treating metabolic liver disease, particularly for treating NAFLD, NASH and/or cirrhosis.

Unless otherwise defined herein, scientific and technical terms used herein shall have the meanings that are commonly understood by those of ordinary skill in the art.

Throughout this specification, the word "comprise" or variations such as "comprises" or "comprising" will be understood to imply the inclusion of a stated integer or component, or of a stated group of integers or components, but not the exclusion of any other integer or component or group of integers or components.

The singular forms "a," "an," and "the" include the plurals unless the context clearly dictates otherwise.

The term "including" is used to mean "including but not limited to." "Including" and "including but not limited to" are used interchangeably.

The terms "patient", "subject," and "individual" may be used interchangeably and refers to a human animal.

The above definition of formula I comprises corresponding compounds present in neutral or charged states. Compounds in charged states are for example present in the form of salts, e.g. pharmaceutically acceptable salts, or in solutions, specifically in aqueous solutions.

As used herein, the term "pharmaceutically acceptable salt" is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", $3^{rd}$ edition, James Swarbrick (Ed.), Informa Healthcare USA (Inc.), NY, USA, 2007, and in *J. Pharm. Sci.* 66: 2 (1977).

The term "agonist" as employed in the context of the invention refers to a substance that activates the receptor type in question, typically by binding to it (i.e. as a ligand).

Throughout this specification, the conventional one letter and three letter codes for naturally occurring amino acids are used, as well as generally accepted abbreviations for other amino acids, such as Aib (α-aminoisobutyric acid), and Ac4c (1-amino-cyclobutanecarboxylic acid). The term "isoGlu" refers to a γ-glutamic acid unit.

Unless otherwise indicated, reference is made to the L-isomeric forms of the amino acids in question.

Additional abbreviations include the following:

NAFL: non-alcoholic fatty liver

NAFLD: non-alcoholic fatty liver disease

NAS: NAFLD activity score

NASH: non-alcoholic steatohepatitis

MRI-PDFF: magnetic resonance imaging proton density fat fraction

The term "therapeutically effective amount" as used herein in the context of the herein-described methods of treatment or other therapeutic interventions according to the invention refers to an amount that is sufficient to cure, ameliorate, alleviate or partially arrest the clinical manifestations of the particular disease, disorder or condition that is the object of the treatment or other therapeutic intervention in question e.g. as measured by established clinical endpoints or other biomarkers (established or experimental), including liver biopsies. A therapeutically relevant amount may be determined empirically by one skilled in the art based on the indication being treated or prevented and the subject to whom the therapeutically relevant amount is being administered. For example, the skilled worker may measure one or more of the clinically relevant indicators of bioactivity described herein, e.g. liver fat content via MRI-PDFF, body weight or NAS (NAFLD activity score). The skilled worker may determine a clinically relevant amount through in vitro or in vivo measurements. Other exemplary measures include fibrosis markers (serum or plasma), weight loss, change in histological scores of NASH or fibrosis, liver fat content reduction, and change of liver enzymes.

An amount adequate to accomplish any or all of these effects is defined as a therapeutically effective amount. The administered amount and the method of administration can be tailored to achieve optimal efficacy. An amount effective for a given purpose will depend, inter alia, on the severity of the disease, disorder or condition that is the object of the particular treatment or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide or pharmaceutically acceptable salt thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. progression to cirrhosis, progression of fibrosis or worsening of NASH, e.g. increase of NAS) relative to the absence of treatment, and is not necessarily meant to imply complete cessation of the relevant disease, disorder or condition.

The terms "prevention" and grammatical variants thereof (e.g., "prevented", "preventing", "prevent") as employed in the present context refer to an approach for hindering or preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of "prevention" may thus be a subject not yet afflicted with the disease or disorder in question. The term "prevention" thus includes inhibiting or slowing the onset of disease relative to the absence of treatment, and is not necessarily meant to imply permanent prevention of the relevant disease, disorder or condition. In a more specific aspect prevention refers to prevention of progression of the liver disease (e.g. progression to cirrhosis, progression of fibrosis or worsening of NASH, e.g. increase of NAS).

$C_{1-4}$ alkyl groups that may be present as a group R in the context of compounds of the present invention include, but are not limited to, $C_{1-3}$ alkyl groups, such as methyl, ethyl, 1-propyl or 2-propyl.

Peg3 refers to the following structural unit comprising units of ethylene glycol:

—NH(CH$_2$)$_2$O(CH$_2$)$_2$OCH$_2$C(O)NH(CH$_2$)$_2$O(CH$_2$)$_2$OCH$_2$C(O)—.

All publications, patents and published patent applications referred to in this application are incorporated by reference herein, specifically the content of WO2015/055801 is incorporated by reference. In case of conflict, the present specification, including its specific definitions, will control.

Each embodiment of the invention described herein may be taken alone or in combination with one or more other embodiments of the invention.

All compounds according to formula I share a sequence identity of at least 22 out of 29 positions. With the restriction that the compounds contain only one Ψ, the possible variations are further limited, such that, effectively, there are only 4 variable positions, leading to a sequence identity of at least 86%. Further, they share the same amidated C-terminus, and the substituent at the Lys residue (Ψ at position 16, 17, 24 or 28) is selected from two distinct alternatives, namely HOOC—(CH$_2$)$_{16}$—(CO)-isoGlu-Peg3-Peg3- and HOOC—(CH$_2$)$_{16}$—(CO)-isoGlu-GSGSGG-. Their structures are shown here (in each case, --- indicates the point of attachment to the side chain of the amino acid component of Ψ (Lys):

HOOC—(CH$_2$)$_{16}$—(CO)-isoGlu-Peg3-Peg3- or
[17-Carboxy-heptadecanoyl]-isoGlu-Peg3-Peg3:

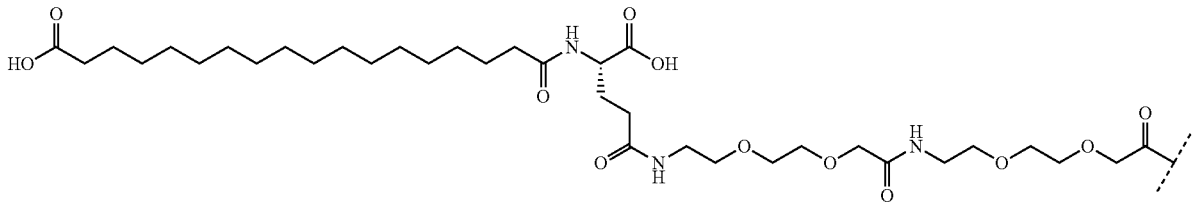

HOOC—(CH$_2$)$_{16}$—(CO)-isoGlu-GSGSGG or
[17-Carboxy-heptadecanoyl]-isoGlu-GSGSGG:

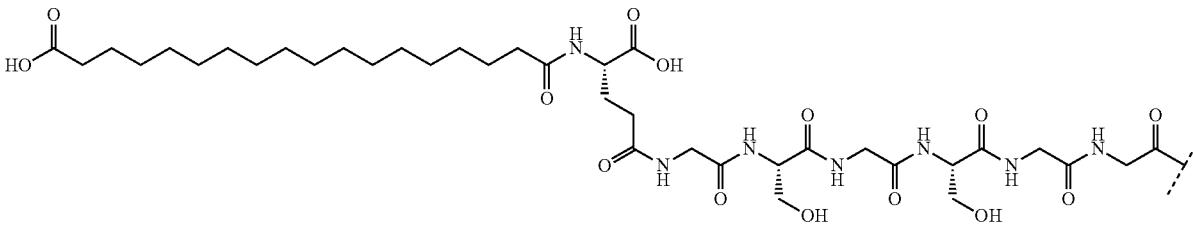

Compounds 1 to 6 (SEQ ID NO.: 3 to SEQ ID NO.: 8, respectively,) are GLP-1 and glucagon receptor agonists as determined by their capability to stimulate intracellular cAMP formation in appropriate assays (e.g. as disclosed in WO2015/055801, Example 2, page 36, Table 1, and Examples 3 and 4, pages 37-40, Table 2 and 3).

Therapeutic Uses

In a first aspect the compounds of the invention may provide treatment and/or prevention options for, inter alia, nonalcoholic steatohepatitis (NASH) with and without fibrosis/cirrhosis and metabolic diseases including obesity and type 2 diabetes, as discussed below.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood), and non-alcoholic fatty liver disease (NAFLD, including NASH with or without fibrosis/cirrhosis).

Without wishing to be bound by any particular theory, it is believed that the compounds of the invention act as dual agonists both on the human glucagon-receptor and the human GLP-1-receptor, abbreviated here as dual GLP-1/glucagon agonists. The dual agonist may combine the effect of glucagon, e.g. on fat metabolism, with the effect of GLP-1, e.g. on blood glucose levels and food intake. They may therefore act to accelerate elimination of excessive adipose tissue, including fatty acid oxidation in the liver, induce sustainable weight loss, and improve steatosis and inflammation in the liver. Therefore, the compounds of the invention may be used to treat NAFLD by reducing liver fat, e.g. by increasing lipid oxidation. Dual GLP-1/glucagon agonists may also act to reduce cardiovascular risk factors, such as high cholesterol, high LDL-cholesterol or low HDL/LDL cholesterol ratios.

The compounds of the present invention can therefore be used in a subject in need thereof as pharmaceutical agents for treating NASH and subsequent fibrosis/cirrhosis, promoting weight loss, treating obesity, as well as associated diseases and health conditions including but not limited to metabolic syndrome linked inflammation, and NASH-related hepatocellular carcinoma. The compounds of the invention may also be used for treatment of conditions caused by or associated with impaired glucose control, including insulin resistance, glucose intolerance, pre-diabetes, increased fasting glucose, type 2 diabetes, hypertension, atherosclerosis, arteriosclerosis, coronary heart disease, peripheral artery disease and stroke, in a subject in need thereof. Some of these conditions can be associated with metabolic syndrome and NASH/NAFLD. However, the effects of the compounds of the invention on these conditions may be mediated in whole or in part via an effect on body weight, or may be independent thereof.

Thus, the invention provides the use of a compound of the invention in the treatment of a condition as described above, in an individual in need thereof. For instance, the compounds described may be used in improving NASH and/or fibrosis, preventing progression to cirrhosis, reverse cirrhosis, and promoting weight loss.

In a specific embodiment, the present invention comprises use of a compound in a method of treatment of a condition of the disease cluster non-alcoholic fatty liver disease, metabolic and alcoholic fatty liver disease, and/or metabolic syndrome, e.g. the treatment and/or prevention of non-alcoholic fatty liver (NAFL), NASH without fibrosis, NASH with fibrosis, NASH related cirrhosis, NASH linked inflammation, overweight and obesity, prediabetes, diabetes, esp. type 2 diabetes, hypertension, atherogenic dyslipidimia, atherosclerosis, arteriosclerosis, coronary heart disease, peripheral artery disease, stroke or microvascular disease in an individual in need thereof.

In another aspect, the invention relates to a compound having the general formula I (as defined above) for use in a method of preventing or treating metabolic liver disease.

In a related aspect, the invention relates to a pharmaceutical composition comprising a compound having the general formula I (as defined above) for use in a method of preventing or treating metabolic liver disease.

In another aspect, the invention relates to a method of preventing or treating metabolic liver disease in a patent in need thereof comprising administering to said patient a therapeutically effective amount of a compound having the general formula I (as defined above).

In a related aspect, the invention relates to a method of preventing or treating metabolic liver disease in a patent in need thereof comprising administering to said patient a pharmaceutical composition comprising a therapeutically effective amount of a compound or a salt thereof having the general formula I (as defined above).

As used herein, the term "metabolic liver disease" refers to alcohol-induced liver disease (also referred to as alcoholic liver disease, ALD), nonalcoholic liver diseases as well as a combination hereof. Metabolic liver disease comprises a spectrum of conditions characterized by hepatic fat deposition, e.g. excessive hepatic fat deposition, including non-alcoholic fatty liver disease (NAFLD), more particularly: non-alcoholic fatty liver (NAFL), non-alcoholic steatohepatitis (NASH), NAFLD-associated liver fibrosis, and NAFLD-associated cirrhosis.

The spectrum of ALD ranges from alcoholic fatty liver (steatosis) via alcoholic steatohepatitis (ASH) to hepatic fibrosis and cirrhosis. Steatosis is the earliest stage of alcoholic liver disease and the most common alcohol-induced liver disorder. It is reversible, if the excessive alcohol intake is stopped in time. ASH is defined by the presence of fatty liver, an inflammatory infiltrate, which mainly consists of polymorphonuclear leukocytes, and hepatocellular damage.

Non-alcoholic liver diseases are related to a metabolic dysregulation in the absence of excessive alcohol intake. A non-alcoholic liver disease of particular interest in the context of the invention is non-alcoholic fatty liver disease (NAFLD). NAFLD is the presence of hepatic steatosis in the absence of other causes for secondary hepatic fat accumulation (e.g., heavy alcohol consumption). Patients with NAFLD have hepatic steatosis, with or without inflammation, hepatocellular damage or fibrosis/cirrhosis.

NAFLD is, in the context of the invention, subdivided into non-alcoholic fatty liver (NAFL), non-alcoholic steatohepatitis (NASH), NAFLD-associated liver fibrosis, and NAFLD-associated cirrhosis. Thus, a patient having NAFLD according to the present invention has to be diagnosed with NAFL or NASH and/or NAFLD-associated liver fibrosis/cirrhosis. Of note, fibrosis can typically be present to various extents in individuals with NASH from mild (histological fibrosis stage F1, Kleiner et al.) to cirrhosis (histological fibrosis stage F4). In NAFL, hepatic steatosis is present without evidence of hepatocellular ballooning and advanced inflammation, whereas in NASH, hepatic steatosis is associated with hepatic inflammation that may be histologically indistinguishable from alcoholic steatohepatitis. According to Ratziu et al (Gastroenterology 2016, vol. 150, pp. 1 147-1 159) and Kleiner and Bedossa (Gastroenterology 2015, vol. 149, pp. 1305-1308), NASH is distinguished from NAFL by the presence of hepatocyte ballooning with some degree of inflammation in addition to steatosis. Other terms that have been used to describe NASH include pseudoalcoholic hepatitis, alcohol-like hepatitis, fatty liver hepatitis, steatonecrosis, and diabetic hepatitis.

Liver fibrosis results from chronic damage to the liver in conjunction with the accumulation of extracellular matrix proteins, which is a characteristic of most types of chronic liver diseases. The main causes of liver fibrosis in industrialized countries include chronic HCV (hepatitis-C-virus) infection, alcohol abuse, and non-alcoholic steatohepatitis (NASH). The accumulation of extracellular matrix proteins distorts the hepatic architecture by forming a fibrous scar, and the subsequent development of nodules of regenerating hepatocytes defines cirrhosis (Bataller and Brenner, J Clin Invest. 2005, vol. 1 15, pp. 209-218).

Non-alcoholic steatohepatitis is a clinical entity characterized by liver biopsy findings that are identical to those seen in alcoholic hepatitis; patients with NASH, however, do not consume alcohol in quantities known to cause liver injury. Patients with NASH are typically middle-aged or older, with asymptomatic hepatomegaly and are diabetic or hyperlipidemic and present with overweight or obesity and present with an unrelated medical problem. Analysis of liver biopsy specimens is the cornerstone of diagnosis; hepatic morphologic findings range from mild fatty degeneration and inflammation to cell degeneration, fibrosis, and cirrhosis with or without the presence of Mallory hyaline bodies.

Patients with NASH have no specific symptoms for a long period of time but may progress to liver cirrhosis or hepatocellular carcinoma (HCC). Accordingly, NAFLD-related cirrhosis and NAFLD-related hepatocellular carcinoma are also referred to herein as sequelae of NASH. The risk of progression from NASH to cirrhosis is particularly high in patients with advanced fibrosis. NAFLD-related cirrhosis is an important risk factor in the further development of the disease into NAFLD-related HCC. However, NAFLD-related HCC may also develop in NASH patients without cirrhosis.

Non-alcoholic fatty liver disease (NAFLD) is seen worldwide and is the most common metabolic liver disorder in Western industrialized countries, where the major risk factors for NAFLD, central obesity, type 2 diabetes mellitus, dyslipidemia, and metabolic syndrome are common. In the United States, studies report a prevalence of NAFLD of 10 to 46 percent, with most biopsy-based studies reporting a prevalence of NASH of 3 to 5 percent. Worldwide, NAFLD has a reported prevalence of 6 to 35 percent (median 20 percent) (Williams C D et al., Gastroenterology. 201 1:140 (1):124-31; Vernon Get al., Alimwent Pharmacol Ther. 201 1:34(3):274-85; Lazo M et al., Am J Epidemiol. 2013; 178(1):38-45).

Most patients with NAFLD are asymptomatic, although some patients with NASH may complain of non-liver specific symptoms, such as fatigue, malaise, and vague right upper abdominal discomfort. Patients are more likely to come to attention because laboratory testing revealed elevated liver aminotransferases, or hepatic steatosis was detected incidentally on abdominal imaging. Once steatohepatitis has developed, the risk of cirrhosis is increased compared with simple steatosis. According to a publication from Bertot and Adams (Int J Mol Sci. 2016; 17(5):774-85), the progression rate of patients with NAFLD to NASH, from NAFLD to NASH with fibrosis, from NASH to NAFLD-related cirrhosis and from NASH with fibrosis to hepatocellular carcinoma is analyzed. There is a clearly increased risk of progression to cirrhosis in patients with NASH and about 25% of patients with NAFLD may progress to NASH within a 3 years' time period. Once NASH is established and depending on additional risk factors, up to 38% percent of patients develop NAFLD related cirrhosis over time.

As mentioned above, one aspect of the invention relates to the use of a compound of formula I or a pharmaceutical composition comprising such a compound in a method of treating non-alcoholic fatty liver disease (NAFLD). More precisely, the disease state to be treated is non-alcoholic fatty liver (NAFL), non-alcoholic steatohepatitis (NASH), NAFLD-associated liver fibrosis or NAFLD-associated cirrhosis.

In more specific aspects, the compound of formula I or the pharmaceutical composition comprising such a compound is for use in a method of preventing or treating non-alcoholic steatohepatitis (NASH). NASH may or may not be associated with different stages of liver fibrosis, including cirrhosis.

In 2005, the Pathology Committee of the NASH Clinical Research Network (CRN) developed the so-called "NAFLD activity score (NAS)" for use in clinical trials (Kleiner et al., Hepatology 2005, vol. 41, pp. 1313-1321). Other scoring systems may also be used to diagnose NAFLD and the severity of its components.

The NAS specifically includes features of active injury that are potentially reversible in the short term. The NAS is defined as the unweighted sum of the subscores for (i) steatosis, (ii) lobular inflammation and (iii) hepatocellular ballooning. Each subscore is graded semi-quantitatively as described in the following Table 1.

TABLE 1

Definition of NAS subscores

| Subscore histological feature | definition | score |
|---|---|---|
| steatosis (0-3) | | |
| grade | low- to medium-power evaluation of parenchymal involvement by steatosis (% of cells) | |
| | <5% | 0 |
| | 5%-33% | 1 |
| | >33%-66% | 2 |
| | >66% | 3 |
| lobular inflammation (0-3) | | |
| | overall assessment of all inflammatory foci | |
| | no foci | 0 |
| | 1 to <2 foci per 200x field | 1 |
| | 2-4 foci per 200x field | 2 |
| | >4 foci per 200x field | 3 |
| hepatocellular ballooning (0-2) | | |
| | no ballooned cells | 0 |
| | few ballooned cells (rare but definite ballooned hepatocytes; cases that are diagnostically borderline included) | 1 |
| | many ballooned cells/prominent ballooning | 2 |

Usually, NAFLD is defined by the presence of steatosis in >5% of hepatocytes, NASH by the presence, in addition, of hepatocellular ballooning of any degree and lobular inflammatory infiltrates of any amount (Bedossa et al., Hepatology 2015, vol. 56, pp. 1751-1759).

Diagnosis of NAFLD and NASH according to the present invention is described in the following Table 2:

TABLE 2

Diagnostic algorithm for NAFL versus NASH according to NAS subscores

| steatosis | (hepatocycte) ballooning | (lobular) inflammation | diagnosis |
|---|---|---|---|
| 0 | 0, 1, 2 | 0, 1, 2, 3 | No NAFLD |
| 1, 2, 3 | 0 | 0 | NAFL |
| 1, 2, 3 | 0 | 1 | NAFL |
| 1, 2, 3 | 0 | 2 | NASH |
| 1, 2, 3 | 0 | 3 | NASH |
| 1, 2, 3 | 1 | 0 | NASH |
| 1, 2, 3 | 1 | 1 | NASH |
| 1, 2, 3 | 1 | 2 | NASH |
| 1, 2, 3 | 1 | 3 | NASH |
| 1, 2, 3 | 2 | 0 | NASH |
| 1, 2, 3 | 2 | 1 | NASH |
| 1, 2, 3 | 2 | 2 | NASH |
| 1, 2, 3 | 2 | 3 | NASH |

Accordingly, in the context of the present invention, a patient is diagnosed as suffering from NAFLD, if at least the subscore for steatosis (sometimes also referred to as the "steatosis subscore" or simply "steatosis score" herein) is >1. NASH can be discriminated from NAFL or simple steatosis by the presence of hepatocyte ballooning (sometimes also referred to as the "ballooning subscore" or simply "ballooning score" herein) with or without some degree of inflammation (sometimes also referred to as the "inflammation subscore" or simply "inflammation score" herein). In this context, NASH resolution has been defined as the disappearance of ballooning (subscore=0), together with either disappearance of lobular inflammation or the persistence of mild lobular inflammation only (subscore=0 or 1) (Kleiner and Bedossa, Gastroenterology 2015, vol 149, pp. 1305-1308). This definition was used for the diagnostic algorithm described in Table 2.

To assess efficacy of the compounds of the invention, not only the NAS, but also the fibrosis score is determined. The fibrosis score may, for example, be determined according to Kleiner et al. (Hepatology 2005, vol. 41, pp. 1313-1321; also referred herein as the "Kleiner fibrosis score"), summarized in the following Table 3.

TABLE 3

Definition of the Kleiner fibrosis score

| Fibrosis | comments | score |
|---|---|---|
| none | | 0 |
| portal/periportal | mild fibrosis | 1 |
| perisinusoidal and portal/periportal | moderate fibrosis between portal areas, but without destruction of the lobular structure | 2 |
| bridging fibrosis | fibrotic bridging between portal areas and between portal areas and center veins | 3 |
| cirrhosis | additionally pseudo-lobules formed | 4 |

Whereas the NAS determines the extent of NAFL and NASH (higher score means higher disease activity), the Kleiner fibrosis score determines the extent of fibrosis progression. A decrease in NAS only is relevant if fibrosis does not further progress. Therefore, a positive response to treatment exists, if no worsening (i.e. increase) or an improvement (lower score) in NAS, in particular disappearance of hepatocyte ballooning (ballooning score=0), is present in the absence of worsening (i.e. increase) of the Kleiner fibrosis score.

Pharmaceutical Compositions

The invention also extends to compositions, such as pharmaceutical compositions, comprising a compound of formula I for use in method of preventing or treating metabolic liver disease, particularly for treating NAFLD and/or NASH. As with all aspects of the invention, it is to be understood that reference to a compound of formula I encompasses reference to compounds in the form of a pharmaceutically acceptable salt.

The compounds of formula I may be formulated as pharmaceutical compositions which are suited for administration, and which typically comprise a therapeutically effective amount of at least one compound of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in injectable form in a device for application, for example in the form of a pen device or an auto-injector containing a liquid-phase (typically aqueous) composition.

Subcutaneous administration is the most common route of application of therapeutic peptides generally, and also seems suitable for the compounds of formula I. For this case a single-use (provides the quantity of the compound for a single dosage unit) or a multiple use (provides the quantity of the compound for more than one dosage unit) device can be used. Suitable devices comprise auto-injector (e.g. for single-use) or pens (e.g. for multiple use) containing a cartridge with a liquid (e.g. aqueous) formulation of the compound.

Dosages

A typical dosage of a compound according to formula I may be in the range from about 0.0005 to about 5 mg/kg body weight per week, e.g. from about 0.001 to about 0.5 mg/kg body weight per week. The exact dosage employed may depend, inter alia, on: the nature and severity of the disease or disorder to be treated, on the sex, age, body weight and general condition of the subject to be treated, on possible other, concomitant, disease or disorder that is undergoing or is to undergo treatment, as well as on other factors that will be known to a medical practitioner of skill in the art.

Combination Therapy

A compound according to formula I may be administered as part of a combination therapy together with another active agent for the treatment of a liver disease, e.g. NAFLD, in particular NAFL, NASH or NAFLD-associated liver fibrosis. In such cases, the two active agents may be given together or separately, e.g. as constituents in the same pharmaceutical composition or formulation, or as separate formulations.

Thus, a peptide of the invention may be used in combination with another pharmaceutically active compound including, but not limited to, compounds selected from the group consisting of a AOC3 inhibitor, sGC activator, FGF21 agonist, GDF15 agonist, HSD17B13 inhibitor, KHK inhibitor, RORc inhibitor, cGAS inhibitor, STING inhibitor, ACC inhibitor, FXR agonist, THR beta agonist, FGF19 agonist, NLRP3 inhibitor, KLB/FGFR1c inhibitor, PNPLA3 inhibitor, Alpha V beta integrin inhibitor, Leukotriene inhibitor, and SGLT2 inhibitor.

In some embodiments, the invention relates to a device comprising a compound according to formula I or a combination as defined above or pharmaceutical composition of the invention, for delivery of the compound to a subject.

Particular Embodiments

Further embodiments of the invention are described:
1. A compound having the general formula I
R—H-X2-QGTFTSDYSKYL-X15-X16-X17-X18-AKDFI-X24-WLE-X28-A-NH$_2$(SEQ ID NO.: 2) (I), wherein
R is selected from H, C$_{1-4}$ alkyl and acetyl;
X2 is selected from Aib and Ac4c;
X15 is selected from Asp and Glu;
X16 is selected from Glu and Ψ;
X17 is selected from Arg and Ψ;
X18 is selected from Ala and Arg;
X24 is selected from Glu and Ψ;
X28 is selected from Ser and Ψ;
wherein the compound contains one and only one Ψ
and wherein said Ψ is a residue of Lys, in which the amino group of the side chain is conjugated to a substituent selected from the group consisting of
HOOC—(CH$_2$)$_{16}$—(CO)-isoGlu-Peg3-Peg3-, and
HOOC—(CH$_2$)$_{16}$—(CO)-isoGlu-GSGSGG-,
for use in a method of preventing or treating metabolic liver disease.
2. The compound according to embodiment 1 for use according to embodiment 1, wherein X2 is Aib.
3. The compound according to embodiment 1 for use according to embodiment 1, wherein X2 is Ac4c.
4. The compound according to any one of embodiments 1 to 3 for use according to embodiment 1, wherein X15 is Asp.
5. The compound according to any one of embodiments 1 to 4 for use according to embodiment 1, wherein X16 is Glu.
6. The compound according to any one of embodiments 1 to 4 for use according to embodiment 1, wherein X16 is Ψ.
7. The compound according to any one of embodiments 1 to 6 for use according to embodiment 1, wherein X17 is Arg.
8. The compound according to any one of embodiments 1 to 6 for use according to embodiment 1, wherein X17 is Ψ.
9. The compound according to any one of embodiments 1 to 8 for use according to embodiment 1, wherein X18 is Ala.
10. The compound according to any one of embodiments 1 to 8 for use according to embodiment 1, wherein X18 is Arg.
11. The compound according to any one of embodiments 1 to 10 for use according to embodiment 1, wherein X24 is Glu.
12. The compound according to any one of embodiments 1 to 10 for use according to embodiment 1, wherein X24 is LP.
13. The compound according to any one of embodiments 1 to 12 for use according to embodiment 1, wherein X28 is Ser.
14. The compound according to any one of embodiments 1 to 12 for use according to embodiment 1, wherein X28 is P.
15. The compound according to any one of embodiments 1 to 14 for use according to embodiment 1, wherein Ψ is Lys(-Peg$_3$-Peg$_3$-isoGlu-(CO)—(CH$_2$)$_{16}$—COOH).
16. The compound according to any one of embodiments 1 to 14 for use according to embodiment 1, wherein Ψ is Lys(-GSGSGG-isoGlu-(CO)—(CH$_2$)$_{16}$—COOH).
17. Embodiment 1, wherein the compound is
H—H-Aib-QGTFTSDYSKYLD-K([17-carboxy-heptadecanoyl]-isoGlu-Peg3-Peg3)-RAAKDFIEWLESA-NH$_2$(Compound 1, SEQ ID NO.: 3).
18. Embodiment 1, wherein the compound is
H—H-Aib-QGTFTSDYSKYLDERAAKDFI-K([17-carboxy-heptadecanoyl]-isoGlu-GSGSGG)-WLESA-NH$_2$(Compound 2 SEQ ID NO.: 4).
19. Embodiment 1, wherein the compound is
H—H-Ac4c-QGTFTSDYSKYLDE-K([17-carboxy-heptadecanoyl]-isoGlu-Peg3-Peg3)-RAKDFIEWLESA-NH$_2$(Compound 3, SEQ ID NO.: 5).
20. Embodiment 1, wherein the compound is H—H-Aib-QGTFTSDYSKYLE-K([17-carboxy-heptadecanoyl]-isoGlu-GSGSGG)-RAAKDFIEWLESA-NH$_2$ (Compound 4, SEQ ID NO.: 6).
21. Embodiment 1, wherein the compound is
H—H-Ac4c-QGTFTSDYSKYLDERAAKDFI-K([17-carboxy-heptadecanoyl]-isoGlu-GSGSGG)-WLESA-NH$_2$ (Compound 5, SEQ ID NO.: 7).
22. Embodiment 1, wherein the compound is
H—H-Ac4c-QGTFTSDYSKYLDERAAKDFIEWLE-K([17-carboxy-heptadecanoyl]-isoGlu-GSGSGG)-A-NH$_2$(Compound 6, SEQ ID NO.: 8).
23. The compound according to any one of embodiments 1 to 22, wherein the compound is in the form of a salt, more specifically in the form of a pharmaceutically acceptable salt.
24. The compound according to any one of embodiments 1 to 23, for use in a method of preventing or treating non-alcoholic fatty liver disease (NAFLD) (including non-alcoholic steatohepatitis (NASH), non-alcoholic fatty liver (NAFL) or NAFLD-associated liver fibrosis and/or cirrhosis).
25. Embodiment 24, wherein the metabolic liver disease is NAFL.
26. Embodiment 24, wherein the metabolic liver disease is NASH, optionally NASH associated with liver fibrosis (e.g. advanced liver fibrosis).
27. Embodiment 24, wherein the metabolic liver disease is NAFLD-associated liver fibrosis, e.g. advanced liver fibrosis (fibrosis stage moderate (F2) and severe (F3)).

28. Embodiment 24 for use in a patient having a NAS score of at least 2.
29. Embodiment 25 for use in a patient having a NAS score of at least 2.
30. Embodiment 26 for use in a patient having a NAS score of at least 2.
31. Embodiment 24 for use in a patient having a NAS score of at least 3.
32. Embodiment 25 for use in a patient having a NAS score of at least 3.
33. Embodiment 26 for use in a patient having a NAS score of at least 3.
34. Embodiment 24 for use in a patient having a NAS score of at least 4.
35. Embodiment 25 for use in a patient having a NAS score of at least 4.
36. Embodiment 26 for use in a patient having a NAS score of at least 4.
37. Embodiment according to any one of 28 to 36, wherein at least 1 point of the NAS score arises from the ballooning subscore.
38. Embodiment according to any one of 28, 30, 31, 33, 34 and 36, wherein at least 1 point of the NAS score arises each from the ballooning and the inflammation subscore.
39. Embodiment according to any one of 28 to 38, wherein the NAS score is biopsy proven.
40. The compound according to any one of embodiments 1 to 23, for use in a method of preventing progression of NAFL, NASH or NAFLD-associated liver fibrosis.
41. Any one of embodiments 24 to 40, wherein the method comprises preventing worsening of one of the NAS subscores (steatosis, inflammation or ballooning).
42. Any one of embodiments 24 to 41, wherein the method comprises preventing worsening of the NAS score.
43. Any one of embodiments 24 to 42, wherein the method comprises improving the steatosis subscore.
44. Any one of embodiments 24 to 43, wherein the method comprises improving the ballooning subscore.
45. Any one of embodiments 24 to 44 for use in a patient who is overweight or obese.
46. Any one of embodiments 24 to 44 for use in a patient who is obese.
47. Any one of embodiments 24 to 44 for use in a patient having a BMI 27 kg/m$^2$.
48. Embodiment 47, wherein the patient has additional obesity related co-morbidities.
49. Embodiment 48, wherein the co-morbidities are selected from the group consisting of type 2 diabetes, hypertension, dyslipidemia, sleep apnea and cardiovascular disease.
50. Any one of embodiments 24 to 44 for use in a patient having a BMI 30 kg/m$^2$.
51. A pharmaceutical composition comprising a compound according to any one of embodiments 1 to 23 and a pharmaceutically acceptable carrier for use in a method of preventing or treating metabolic liver disease.
52. A pharmaceutical composition comprising a compound according to any one of embodiments 1 to 23 and a pharmaceutically acceptable carrier for use in a method of treating NAFLD (including NASH, NAFL and NAFLD-associated liver fibrosis and/or cirrhosis).
53. A pharmaceutical composition comprising a compound according to any one of embodiments 1 to 23 and a pharmaceutically acceptable carrier for use in a method of treating NAFL, NASH or NAFLD-associated liver fibrosis.
54. A pharmaceutical composition comprising a compound according to any one of embodiments 1 to 23 and a pharmaceutically acceptable carrier for use in a method of treating NASH.
55. A pharmaceutical composition comprising a compound according to any one of embodiments 1 to 23 and a pharmaceutically acceptable carrier for use according to any one of embodiments 28 to 39.
56. A pharmaceutical composition comprising a compound according to any one of embodiments 1 to 23 and a pharmaceutically acceptable carrier for use in method of preventing or treating NASH, optionally NASH associated with liver fibrosis (e.g. advanced liver fibrosis), in a patient having a NAS score of at least 4.
57. A method of preventing or treating metabolic liver disease in a patient in need thereof, comprising administering to said patient a therapeutically effective amount of a compound according to any one of embodiments 1 to 23.
58. A method of treating NASH, particularly NASH associated with liver fibrosis, in a patient in need thereof, comprising administering to said patient a therapeutically effective amount of a compound according to any one of embodiments 1 to 23.

EXAMPLES

Example 1: Effect on Fatty Liver in DIO Mice

Method

Male $C_{57}BL/6J$ mice were obtained from Charles River (Sulzfeld, Germany) at the age of 6-7 weeks. Upon arrival at the animal facility, they were fed ad libitum with pelleted diet no. 3808 from Provimi Kliba (Kaiseraugst, Switzerland) and had free access to tab water. After one week, the animals were put on a high fat diet with 45% of metabolizable energy coming from fat (ssniff EF R/M acc. D12451 (I) mod.; ssniff Spezialdiäten GmbH, Soest, Germany). After 25 weeks on high fat diet, the animals were randomized into groups with similar average body weight (day 0). An additional control group (lean control) was used in the study consisting of animals that had remained on standard low fat diet (diet no. 3808 from Provimi Kliba). The age of the mice was 32-33 weeks at start of compound treatment.

All animals received twice daily subcutaneous injections, the first at 7 AM in the morning and the second 8 h later at 3 PM in the afternoon. Compound 5 was dosed once daily at 7 AM by subcutaneous injection followed by an additional vehicle injection 8 h later. Liraglutide was dosed twice daily at 7 AM and 3 PM by subcutaneous injection. Control animals (either on high fat diet or lean controls) received a twice daily injection of vehicle (25 mM PBS). Body weight was measured daily before the administration in the morning.

First dosing occurred on day 1, last dosing occurred on day 28. Animals were sacrificed immediately after the final blood sampling on day 29 by cervical dislocation. An aliquot of about 100 mg from the left lateral liver lobe was used for measurement of liver triglycerides.

ALT (alanine-aminotransferase) in plasma was measured using an automated clinical analyser (Cobas Integra 400 plus; Roche Diagnostics, Mannheim, Germany). For determination of liver triglycerides, 100 mg tissue from the left lateral lobe was extracted with 1 ml isopropanol using Fastprep tubes (Mp Biomedicals). Triglycerides in the supernatant were measured using an automated clinical analyser (Cobas Integra 400 plus; Roche Diagnostics, Mannheim, Germany).

Results

Liver fat was measured on day 29 at the end of the study after a 12 h fast (FIG. 1a). The mean liver triglyceride content of the vehicle-treated animals on high fat diet indicates liver steatosis (203 mg/g liver) when compared to lean controls (53 mg/g liver). Liver triglycerides were significantly reduced by 63 mg/g and −146 mg/g after treatment with 10 and 30 nmol/kg qd of compound 5 (40 μg/kg and 120 μg/kg, resp.). Liraglutide (10 nmol/kg bid, 40 μg/kg bid) reduced liver triglycerides by −27 mg/g which was significantly less than with the 10 nmol/kg qd dose of compound 5. Overall, compound 5 shows a larger effect on lowering liver triglycerides compared to liraglutide.

The transaminase ALT which is primarily expressed in liver showed strongly elevated mean levels in plasma of vehicle-treated animals on high fat diet (404 U/l; FIG. 1b) when compared to lean controls (38 U/l), indicating steatosis-induced liver cell damage in this DIO mouse model. ALT was significantly reduced by 250 U/l and −347 U/l after treatment with 10 and 30 nmol/kg qd of compound 5. Liraglutide reduced ALT by −188 U/L which was significantly less than with the 10 nmol/kg qd dose of compound 5. The more profound reduction of ALT in plasma by compound 5 is concomitant with its larger reduction of liver triglycerides than liraglutide.

Example 2: Efficacy in a Murine Diet-Induced NASH Model

Method

Compound 5 and liraglutide were investigated in a mouse model of NASH (murine diet-induced NASH model) as described in Kristiansen et al (World Journal of Hepatology 2016, vol. 8, pp. 673-684). $C_{57}BL/6J$ mice were given ad libitum access to a diet (D09100301, Research Diet, United States) high in fat (40%, of these 18% trans-fat), carbohydrates (40%, of these 20% fructose) and cholesterol (2%) that has previously been described as AMLN diet (Clapper et al., Am J Physiol Gastrointest Liver Physiol 2013, vol. 305, pp. G483-G495). A control group was kept on regular rodent chow (Altromin 1324, Brogaarden, Denmark). After 26 weeks on the diet, a liver biopsy was performed for histological assessment of NASH and fibrosis at baseline. For this purpose, mice were anesthetized by inhalation anesthesia using isoflurane (2-3%). A small abdominal incision was made in the midline and the left lateral lobe of the liver was exposed. A cone shaped wedge of liver tissue (approximately 50 mg) was excised from the distal portion of the lobe and fixated in 10% neutral buffered formalin (4% formaldehyde) for histology. The cut surface of the liver was instantly electrocoagulated using bipolar coagulation (ERBE VIO 100 electrosurgical unit). The liver was returned to the abdominal cavity, the abdominal wall was sutured, and the skin was closed with staplers. For postoperative recovery mice received carprofen (5 mg/kg) administered subcutaneously on OP day and post-OP day 1 and 2.

For histological assessment, slides with paraffin embedded sections were de-paraffinated in xylene and rehydrated in series of graded ethanol. For Hematoxylin & Eosin (H&E) staining, the slides were incubated in Mayer's Hematoxylin (Dako), washed in tap water, stained in Eosin Y solution (Sigma-Aldrich), hydrated, mounted with Pertex and then allowed to dry before scanning. For Sirius red staining, the slides were incubated in Weigert's iron hematoxylin (Sigma-Aldrich), washed in tap water, stained in Picro-sirius red (Sigma-Aldrich) and washed twice in acidified water. Excess water was removed by shaking the slides and the slides were then hydrated in three changes of 100% ethanol, cleared in xylene and mounted with Pertex and allowed to dry before scanning. Histological scoring was performed by a pathologist blinded to the study. NAFLD activity score and fibrosis score were determined according to the clinical criteria outlined by Kleiner et al (Hepatology 2005, vol. 14, pp. 1313-1321).

Animals were randomized into different treatment groups according to body weight and extent of fibrosis. Treatment period was eight weeks during which animals remained on the AMLN diet. Compounds were given by once-daily subcutaneous injection. Vehicle-treated animals on AMLN diet and non-treated animals on regular rodent chow were included as controls. Group sizes were between 10 and 14 animals.

After treatment, terminal liver samples were collected and analyzed as for the pre-biopsy.

Results

Compound 5 (daily doses of 80 μg/kg, 120 μg/kg and 160 μg/kg) and liraglutide (daily dose of 400 μg/kg) were investigated in the diet-induced NASH model. At baseline, after 26 weeks on the AMLN diet, the body weight of the animals was between 38 and 40 g and significantly higher than in lean controls but not significantly different between the treatment groups. After 8 weeks of treatment, a significant body weight loss of a similar degree versus vehicle was achieved with all doses of compound 5 and liraglutide. The body weight was significantly different between compound 5 at 120 μg/kg qd (32.0 g) or 160 μg/kg qd (31.2 g) and liraglutide (33.8 g) (FIG. 2a).

After 8 weeks of treatment, the NAFLD activity score (NAS) was significantly lower with all doses of compound 5 and liraglutide than in the vehicle group (6.2). The mean rank of compound 5 at 120 μg/kg qd (3.3) or 160 μg/kg qd (3.2) was significantly lower than the mean rank of the liraglutide group (4.1) (FIG. 2b). Treatment with compound 5 at all doses or liraglutide also resulted in a significant improvement in NAS versus baseline compared to vehicle-treated animals (FIG. 2c). Whereas NAS increased by 0.9 points in the vehicle group, it decreased 2.0 points, 2.5 points and 2.4 points with compound 5 at 80, 120 and 160 μg/kg qd, respectively. The decrease with liraglutide of 1.8 points was not statistically different from the baseline reductions in NAS achieved with compound 5. The vehicle-corrected NAS baseline change is shown in FIG. 2d.

The individual components of NAS (steatosis, inflammation and hepatocyte ballooning scores are shown in FIG. 2e. After 8 weeks of treatment, steatosis score was 3 in vehicle-treated animals while it was significantly reduced to 1.5, 1.3 and 1.2 with doses of 80, 120 and 160 μg/kg qd of compound 5. Liraglutide significantly reduced the steatosis score to 2.1. Of note, all reductions achieved with compound 5 were statistically significant versus the treatment effect of liraglutide. Inflammation score was 2.3 in vehicle-treated animals and it was moderately and not statistically significant reduced to 2 by all doses of compound 5. Liraglutide significantly reduced the inflammation score to 1.9. However, the effects of compound 5 and liraglutide on the inflammation score were not statistically different from each other. Mean rank of the ballooning score was 0.9 in vehicle-treated animals. No ballooning cells were detected in animals treated with compound 5 at any dose (ballooning score 0) and only in few animals treated with liraglutide (ballooning score 0.1) with no statistical difference between compound 5 and liraglutide.

The fibrosis score moderately increased by 0.2 in vehicle-treated animals while it remained unchanged with compound 5 at 80 μg/kg qd and significantly decreased by 0.1 and 0.2 with 120 and 160 μg/kg qd of compound 5. The baseline change of the fibrosis score with liraglutide was 0.1 and not significantly different from the reductions seen with compound 5 (FIG. 2f).

The results show that a representative example of the dual GLP-1/glucagon receptor agonists of the present invention profoundly reduces body weight and NAS in DIO-NASH mice. The improvement of the NAFLD activity score is mainly driven by improvements of liver steatosis. The reduction of body weight and liver steatosis is more pronounced than with liraglutide.

Example 3: Estimate of Pharmacokinetic Parameters

Pharmacokinetic parameters of the test compounds were determined after intravenous administration to Han/Wistar rats. The acylated GLP-1 analogue semaglutide was also tested for comparison purposes.

Male Wistar rats were obtained from Charles River (Germany) weighing approximately 180 to 210 g at time of arrival at the test facility. Rats were caged in European standard rat cages type IV with light cycle of 12-hour dark and 12-hour light. During the study rats were housed in standard rat cages type III. Both diet Altromin 1324 (Altromin, Germany) and water was administered ad libitum during the whole experimental period. The animals were housed in the test facility for at least 4 days in order to assure proper acclimatization.

The compounds were first dissolved in 0.1% aqueous ammonia to a nominal concentration of 2 mg/ml, and then diluted to the desired dosing strength (10 μM) in sterile PBS containing 25 mM phosphate buffer, pH 7.4. Intravenous injections corresponding to 20 nmol/kg were given via a lateral tail vein.

Blood samples (200 μl) were collected from the periorbital plexus at time points 0.08, 0.25, 0.5, 1, 2, 4, 8, 24, 32 and 48 h post dosing into K3EDTA tubes and centrifuged for 5 minutes at 4° C. within 20 minutes of sampling. Plasma samples (>100 μl) were transferred to 96-well PCR plates, immediately frozen and kept at −20° C. until analysed for plasma concentration for the respective GLP-1-glucagon compound using LC-MS/MS. Individual plasma concentration-time profiles were analysed by a non-compartmental approach using ToxKin™ version 3.2 (Unilog IT Services), and the resulting pharmacokinetic parameters were determined. See Table 4.

TABLE 4

| Compound | Clearance (ml/min/kg) | Terminal half-life (h) | Mean Residence Time (h) |
|---|---|---|---|
| 1 | 0.11 | 9.1 | 13.6 |
| 2 | 0.056 | 23.4 | 28.7 |
| 3 | 0.11 | 13.7 | 17.6 |
| 5 | 0.0595 | 22.8 | 28.5 |
| 6 | 0.0997 | 18.1 | 23.7 |

Example 4: Clinical Trial Protocol Synopsis to Evaluate Efficacy, Safety and Tolerability of Multiple Subcutaneous (s.c.) Doses of Compound 5 in Patients with NASH and Fibrosis Trial Endpoints The primary endpoint is the improvement (yes/no) from baseline in liver histological findings based on liver biopsy after 48 weeks of treatment in patients with NASH (NAS 4, fibrosis F1-F3).

Improvement in histological findings is defined as a composite of:
Improvement in NASH:
Decrease of at least two points in NAS, with at least one point decrease in NAS sub-score for lobular inflammation or ballooning and
no worsening of fibrosis, defined as an absence of any increase in the fibrosis stage
Secondary efficacy endpoints include:
Improvement of liver fat content (yes/no) defined as at least 30% relative reduction in liver fat content after 48 weeks of treatment compared to baseline assessed by magnetic resonance imaging proton density fat fraction measurement (MRI-PDFF)
Absolute and relative change of liver fat content from baseline after 48 weeks of treatment assessed by MRI-PDFF
Improvement of fibrosis (yes/no) defined as at least one stage decrease in fibrosis stage after 48 weeks of treatment assessed by liver biopsy
Absolute change from baseline in NAS after 48 weeks of treatment assessed by liver biopsy
Trial Design
Multi-center, randomised, dose-ranging, double blind, placebo-controlled, parallel-group trial
Total Number of Patients Randomised
240 patients
Number of Patients on Each Treatment
60 patients on Compound 5: 2.4 mg (Group 1)
60 patients on Compound 5: 4.8 mg (Group 2)
60 patients on Compound 5: 6.0 mg (Group 3)
60 patients on placebo (Group 4)
Diagnosis
Non-alcoholic steatohepatitis (NASH) and fibrosis
Main In— and Exclusion Criteria
Inclusion criteria:
Male or female patients 18 years (or who are of legal age in countries where that is greater than 18 years) and 80 years of age at time of consent.
Diagnosis of NASH (NAS 4, with at least 1 point in inflammation and ballooning each) and fibrosis stage F1-F3 proven by a biopsy conducted during the screening period or by a historical biopsy conducted within the last 6 months prior to randomization and stable body weight defined as less than 5% self-reported change in body weight between the historical biopsy and randomization, if a historical biopsy is used.
Liver fat fraction 8% measured by MRI-PDFF and liver stiffness >6.0 kPa measured by FibroScan® at screening visit (if biopsy is scheduled during the screening period MRI-PDFF and FibroScan® assessments have to be performed prior to the biopsy).
Patients willing and able to undergo liver biopsies per protocol as judged by the Investigator.
BMI≥25 kg/m2 and a body weight≥70 kg at Visit 1.

Exclusion Criteria:

Current or history of significant alcohol consumption (defined as intake of >210 g/week in males and >140 g/week in females on average over a consecutive period of more than 3 months) or inability to reliably quantify alcohol consumption based on Investigator judgement within the last 5 years.

Intake of medications historically associated with liver injury, hepatic steatosis or steatohepatitis within 12 weeks prior to Visit 1. Intake of restricted medications or any medications considered likely to interfere with the safe conduct of the trial.

History of other forms of chronic liver disease (e.g. viral hepatitis, autoimmune liver disease, primary biliary sclerosis, primary sclerosing cholangitis, Wilson's disease, hemochromatosis, A1At deficiency, history of liver transplantation).

Suspicion, diagnosis or history of hepatocellular carcinoma (HCC), or any documented active or suspected malignancy or history of malignancy within 5 years prior to screening, except appropriately treated basal cell carcinoma of the skin or in situ carcinoma of uterine cervix.

Diagnosis of a serious or unstable disease including hepatic (other than NASH), renal, gastroenterologic, respiratory, cardiovascular (including ischemic heart disease), endocrinologic, neurologic, psychiatric, immunologic, or hematologic disease and other conditions that, in the clinical judgment of the Investigator, are likely to interfere with the analyses of safety and efficacy in this trial. Patients with a history of organ transplantation except for corneal transplantation and patients with an expected life expectancy of less than 2 years are also excluded.

Test Product(s)

Solution for injection Compound 5: 0.6 mg/mL, 1.8 mg/mL, 3.6 mg/mL, 4.8 mg/mL and 6.0 mg/mL Pre-filled syringes, 0.5 mL fill volume Dose Group 1: Starting dose of 0.3 mg followed by a dose escalation up to the maintenance dose of 2.4 mg, two pre-filled syringes once weekly Group 2: Starting dose of 0.3 mg followed by a dose escalation up to the maintenance dose of 4.8 mg, two pre-filled syringes once weekly Group 3: Starting dose of 0.3 mg followed by a dose escalation up to the maintenance dose of 6.0 mg, two pre-filled syringes once weekly Mode of administration: Subcutaneous, s.c.

Comparator product: Group 4: Placebo

Dose: Matching mode of administration: Subcutaneous, s.c.

Duration of Treatment 48 weeks of treatment consisting of up to 24 weeks dose escalation period and at least 24 weeks maintenance period

What is claimed is:

1. A method for preventing or treating a metabolic liver disease, comprising administering to a patient in need thereof a therapeutically effective amount of H—H-Ac4c-QGTFTSDYSKYLDERAAKDFI-K([17-carboxy-heptadecanoyl]-isoGlu-GSGSGG)-WLESA-NH$_2$ (Compound 5, SEQ ID NO.: 7),
   wherein the metabolic liver disease is non-alcoholic steatohepatitis (NASH) associated with liver fibrosis and wherein the patient is diagnosed as having a NAFLD activity score (NAS) of at least 4 and, optionally, as having liver fibrosis.

2. The method according to claim 1, wherein at least 1 point of the NAS arises each from the ballooning and the inflammation subscore.

3. A method of preventing or treating a metabolic liver disease, the method comprising administering to a patient in need thereof a pharmaceutical composition comprising a therapeutically effective amount of H—H-Ac4c-QGTFTSDYSKYLDERAAKDFI-K([17-carboxy-heptadecanoyl]-isoGlu-GSGSGG)-WLESA-NH$_2$ (Compound 5, SEQ ID NO.: 7),
   GSGSGG wherein the metabolic liver disease is non-alcoholic steatohepatitis (NASH) associated with liver fibrosis and wherein the patient is diagnosed as having a NAFLD activity score (NAS) of at least 4 and, optionally, as having liver fibrosis.

4. The method according to claim 3, wherein at least 1 point of the NAS arises each from the ballooning and the inflammation subscore.

5. A method of treating a metabolic liver disease, the method comprising administering to a patient in need thereof a pharmaceutical composition comprising a therapeutically effective amount of H—H—Ac4c—QGTFTSDYSKYLDERAAKDFI-K([17-carboxy-heptadecanoyl]-isoGlu-GSGSGG)-WLESA-NH2 (Compound 5, SEQ ID NO.: 7), wherein the metabolic liver disease is non-alcoholic steatohepatitis (NASH) associated with liver fibrosis and wherein the patient is diagnosed as having a NAFLD activity score (NAS) of at least 4 and, optionally, as having liver fibrosis.

6. The method according to claim 5, wherein at least 1 point of the NAS arises each from the ballooning and the inflammation subscore.

7. A method for preventing or treating a metabolic liver disease, comprising administering to a patient in need thereof a therapeutically effective amount of a pharmaceutically acceptable salt of H—H—Ac4c—QGTFTSDYSKY-LDERAAKDFI-K([17-carboxy-heptadecanoyl]-isoGlu-GSGSGG)-WLESA-NH$_2$ (Compound 5, SEQ ID NO.: 7), wherein the metabolic liver disease is non-alcoholic steatohepatitis (NASH) associated with liver fibrosis and wherein the patient is diagnosed as having a NAFLD activity score (NAS) of at least 4 and, optionally, as having liver fibrosis.

8. The method according to claim 7, wherein at least 1 point of the NAS arises each from the ballooning and the inflammation subscore.

\* \* \* \* \*

UNITED STATES PATENT AND TRADEMARK OFFICE
CERTIFICATE OF CORRECTION

PATENT NO. : 11,813,312 B2
APPLICATION NO. : 17/237210
DATED : November 14, 2023
INVENTOR(S) : Leo Thomas Page 1 of 1

It is certified that error appears in the above-identified patent and that said Letters Patent is hereby corrected as shown below:

In the Claims

In Claim 3, at Column 29, Lines 42-44, the text "(Compound 5, SEQ ID NO.: 7), GSGSGG wherein the metabolic liver disease" should be replaced with the text "(Compound 5, SEQ ID NO.: 7), wherein the metabolic liver disease".

Signed and Sealed this
Sixteenth Day of April, 2024

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: SITE
<222> LOCATION: 20
<223> OTHER INFORMATION: The epsilon amino group has the following
      substituent: (S)-4-Carboxy-4-hexadecanoyl-amino-butyryl-

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Leu Ala Trp Leu Val Arg Gly Arg Gly
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: generic formula I
<220> FEATURE:
<221> NAME/KEY: VARIANT
<222> LOCATION: 2
<223> OTHER INFORMATION: Xaa is selected from the group consisting of
      Aib and Ac4c
<220> FEATURE:
<221> NAME/KEY: VARIANT
<222> LOCATION: 15
<223> OTHER INFORMATION: Xaa is selected from the group consisting of
      Asp and Glu
<220> FEATURE:
<221> NAME/KEY: VARIANT
<222> LOCATION: 16
<223> OTHER INFORMATION: Xaa is selected from the group consisting of
```

```
          Glu and Psi
<220> FEATURE:
<221> NAME/KEY: VARIANT
<222> LOCATION: 17
<223> OTHER INFORMATION: Xaa is selected from the group consisting of
      Arg and Psi
<220> FEATURE:
<221> NAME/KEY: VARIANT
<222> LOCATION: 18
<223> OTHER INFORMATION: Xaa is selected from the group consisting of
      Ala and Arg
<220> FEATURE:
<221> NAME/KEY: VARIANT
<222> LOCATION: 24
<223> OTHER INFORMATION: Xaa is selected from the group consisting of
      Glu and Psi
<220> FEATURE:
<221> NAME/KEY: VARIANT
<222> LOCATION: 28
<223> OTHER INFORMATION: Xaa is selected from the group consisting of
      Ser and Psi

<400> SEQUENCE: 2

His Xaa Gln Gly Thr Phe Thr Ser Asp Tyr Ser Lys Tyr Leu Xaa Xaa
1               5                   10                  15

Xaa Xaa Ala Lys Asp Phe Ile Xaa Trp Leu Glu Xaa Ala
            20                  25

<210> SEQ ID NO 3
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Aib
<220> FEATURE:
<221> NAME/KEY: SITE
<222> LOCATION: 16
<223> OTHER INFORMATION: The epsilon amino group of Lys is substituted
      with ([17-carboxy-heptadecanoyl]-isoGlu-Peg3-Peg3)-

<400> SEQUENCE: 3

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 4
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Aib
<220> FEATURE:
<221> NAME/KEY: SITE
<222> LOCATION: 24
<223> OTHER INFORMATION: The epsilon amino group of Lys is substituted
      with ([17-carboxy-heptadecanoyl]-isoGlu-Peg3-Peg3)-

<400> SEQUENCE: 4

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25
```

```
<210> SEQ ID NO 5
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Ac4c
<220> FEATURE:
<221> NAME/KEY: SITE
<222> LOCATION: 17
<223> OTHER INFORMATION: The epsilon amino group of Lys is substituted
      with ([17-carboxy-heptadecanoyl]-isoGlu-Peg3-Peg3)-

<400> SEQUENCE: 5

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Aib
<220> FEATURE:
<221> NAME/KEY: SITE
<222> LOCATION: 16
<223> OTHER INFORMATION: The epsilon amino group of Lys is substituted
      with ([17-carboxy-heptadecanoyl]-isoGlu-GSGSGG)-

<400> SEQUENCE: 6

His Xaa Gln Gly Thr Phe Thr Ser Asp Tyr Ser Lys Tyr Leu Glu Lys
1               5                   10                  15

Arg Ala Ala Lys Asp Phe Ile Glu Trp Leu Glu Ser Ala
            20                  25

<210> SEQ ID NO 7
<211> LENGTH: 29
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Ac4c
<220> FEATURE:
<221> NAME/KEY: SITE
<222> LOCATION: 24
<223> OTHER INFORMATION: The epsilon amino group of Lys is substituted
      with ([17-carboxy-heptadecanoyl]-isoGlu-GSGSGG)-

<400> SEQUENCE: 7

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25

<210> SEQ ID NO 8
<211> LENGTH: 29
```

```
<212> TYPE: PRT
<213> ORGANISM: Artificial Sequence
<220> FEATURE:
<223> OTHER INFORMATION: glucagon analogue
<220> FEATURE:
<221> NAME/KEY: SITE
<222> LOCATION: 2
<223> OTHER INFORMATION: Ac4c
<220> FEATURE:
<221> NAME/KEY: SITE
<222> LOCATION: 28
<223> OTHER INFORMATION: The epsilon amino group of Lys is substituted
      with ([17-carboxy-heptadecanoyl]-isoGlu-GSGSGG)-

<400> SEQUENCE: 8

His Xaa Gln Gly Thr Phe Thr Ser Asp Tyr Ser Lys Tyr Leu Asp Glu
1               5                   10                  15

Arg Ala Ala Lys Asp Phe Ile Glu Trp Leu Glu Lys Ala
            20                  25
```